US011369760B2

(12) United States Patent
Huang

(10) Patent No.: US 11,369,760 B2
(45) Date of Patent: Jun. 28, 2022

(54) INHALATION ATOMIZER COMPRISING A BLOCKING FUNCTION AND A COUNTER

(71) Applicant: ANOVENT PHARMACEUTICAL (U.S.), LLC, Newark, NJ (US)

(72) Inventor: Cai Gu Huang, Shrewsbury, MA (US)

(73) Assignee: ANOVENT PHARMACEUTICAL (U.S.), LLC, Newark, NJ (US)

( * ) Notice: Subject to any disclaimer, the term of this patent is extended or adjusted under 35 U.S.C. 154(b) by 0 days.

(21) Appl. No.: 15/658,431

(22) Filed: Jul. 25, 2017

(65) Prior Publication Data

US 2019/0030268 A1 Jan. 31, 2019

Related U.S. Application Data

(60) Provisional application No. 62/494,875, filed on Aug. 24, 2016.

(51) Int. Cl.

| | |
|---|---|
| ***A61M 15/00*** | (2006.01) |
| ***A61K 31/439*** | (2006.01) |
| ***A61K 31/167*** | (2006.01) |
| ***A61K 31/4704*** | (2006.01) |
| ***A61K 31/40*** | (2006.01) |
| ***A61K 31/58*** | (2006.01) |
| ***A61K 31/46*** | (2006.01) |
| ***A61K 31/538*** | (2006.01) |
| ***A61K 9/00*** | (2006.01) |

(Continued)

(52) U.S. Cl.

CPC ....... *A61M 15/0081* (2014.02); *A61K 9/0073* (2013.01); *A61K 31/137* (2013.01); *A61K 31/167* (2013.01); *A61K 31/40* (2013.01); *A61K 31/439* (2013.01); *A61K 31/46* (2013.01); *A61K 31/4704* (2013.01); *A61K 31/538* (2013.01); *A61K 31/58* (2013.01); *A61M 11/007* (2014.02); *A61M 15/009* (2013.01); *A61M 15/0065* (2013.01); *A61M 15/0073* (2014.02); *A61M 2205/27* (2013.01)

(58) Field of Classification Search

CPC ............ A61M 15/0081; A61M 11/007; A61M 15/0073; A61M 15/0065; A61M 15/009; A61M 2205/27; A61K 9/0073; A61K 31/137; A61K 31/167; A61K 31/40; A61K 31/439; A61K 31/46; A61K 31/4704; A61K 31/538; A61K 31/58

See application file for complete search history.

(56) References Cited

U.S. PATENT DOCUMENTS 6,149,054 A * 11/2000 Cirrillo .................. G06M 1/22 235/34
7,621,273 B2 * 11/2009 Morton ............ A61M 15/0065 128/205.23

(Continued)

*Primary Examiner* — Steven O Douglas
(74) *Attorney, Agent, or Firm* — Parker Poe Adams & Bernstein LLP

(57) ABSTRACT

The invention is directed to an inhalation atomizer comprising a counter and a blocking function. Counter rotates each time the atomizer is actuated. The blocking function includes a first protrusion on the counter and a second protrusion on a lower unit of the atomizer. Once the predetermined number of actuations has been achieved, the first protrusion encounters the second protrusion and prevents further rotation of the counter so that the atomizer is blocked from further use.

14 Claims, 6 Drawing Sheets

Figure 1:
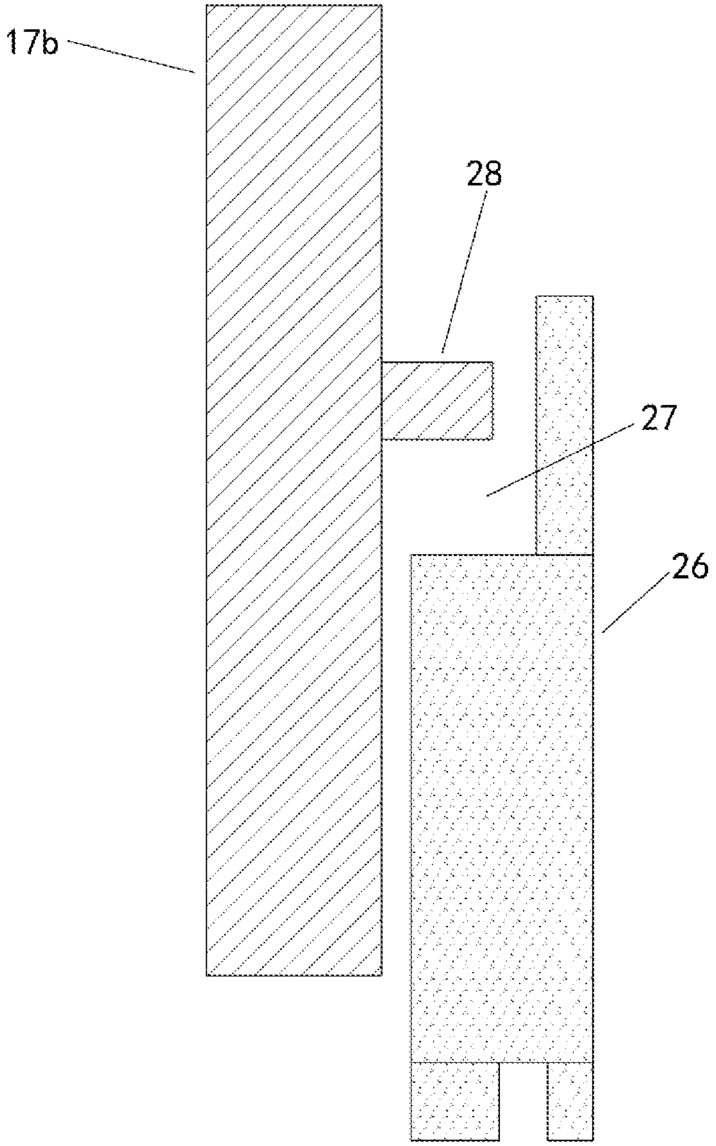

(51) Int. Cl.
*A61M 11/00* (2006.01)
*A61K 31/137* (2006.01)

(56) References Cited

U.S. PATENT DOCUMENTS

| | | | | |
|---|---|---|---|---|
| 9,724,482 | B2 * | 8/2017 | Bach | A61M 15/0065 |
| 9,744,313 | B2 * | 8/2017 | Besseler | A61M 15/00 |
| 10,124,125 | B2 * | 11/2018 | Bach | A61M 15/0065 |
| 10,722,666 | B2 * | 7/2020 | Eicher | A61M 15/0021 |

* cited by examiner

INHALATION ATOMIZER COMPRISING A BLOCKING FUNCTION AND A COUNTER

This application claims the benefit of priority to U.S. Provisional Patent Application Ser. No. 62/494,875 filed on Aug. 24, 2016, the disclosure of which is hereby incorporated by reference.

FIELD OF THE INVENTION

The current invention refers to an inhalation atomizer comprising a block function through a locking mechanism and a counter. After a predetermined number of actuations, the atomizer can be properly blocked by the locking mechanism. The inhalation atomizer has a substitutable and insertable container, a nozzle system and a pressure generator along with a drive spring. The number of actuations of the device can be counted by a mechanical counter.

BACKGROUND OF THE INVENTION

WO-93/21980 discloses a metered-dose inhaler, wherein the inhalation dose of a drug substance is introduced by means of a hand-operated device, from a supply of the drug substance contained in the inhaler, into a chamber from which the dose is expelled with the current of air which the user sucks in through the inhaler as they breathe in. The metered-dose inhaler is fitted with a counter which comprises a rotatable screw spindle and a rod, one end of which engages in the form of a nose in the thread of the screw spindle. The rod moves parallel to the screw spindle as the rotation of the spindle increases. The counter indicates, by means of the position of the nose-like end of the rod, the number of doses which have already been taken out of the supply of drug substance, or those which can still be taken out. The other end of the rod is movably held in a guide shaft into which the rod extends more deeply as the rotation of the screw spindle increases. As soon as the supply of the drug substance in the inhaler is coming to an end, the nose-like end of the rod engaging in the screw spindle reaches that part of the spindle which has a number of courses of thread having a greater pitch than the rest of the screw spindle. As a result, on each rotation of the screw spindle, the rod moves along faster than before. The other end of the rod meanwhile bears on a flexible lever, and further actuation of the metered-dose inhaler is prevented.

WO-97/20590 discloses a locking stressing mechanism for a spring-actuated output drive. WO-97/24586 discloses a mechanical counter for a metering device. WO-97/12687 describes a device for generating high pressure in a fluid in a miniature arrangement provided with a locking stressing mechanism and a counter. The apparatus is used to atomize a fluid to produce an inhalable aerosol. WO-01/64268 describes a needleless injector which contains a locking stressing mechanism.

The components of device equipment described above are intended for repeated use, e.g. for repeated atomization of a given amount of liquid to produce an aerosol for inhalation into the lungs, or for needleless injection of a given quantity of liquid underneath the skin of humans or animals. The quantity of liquid atomized or injected may contain a therapeutically active sub stance.

U.S. Pat. No. 7,396,341 discloses a blocking device for an inhalation apparatus which comprises a locking-stressing-mechanism with an operating spring and a spring transfer member in which is accommodated a piston which is mounted to be moveable in a cylinder, and these components are housed in a two part housing which comprises an upper housing part and a lower housing part, said upper housing part having an inner wall and said lower housing part having an outer wall, and the two parts are mounted to be rotatable relative to each other, and said operating spring is tensioned by means of a screw thrust gear by manually rotating said two housing parts relative to each other, and at the same time as said housing parts are rotated relative to each other a mechanical counter is actuated which comprises a threaded spindle and a slider, and said threaded spindle is mounted in said wall of the lower housing part, and said slider is moved along said spindle by an amount which depends on the number of rotations of said two housing parts relative to each other, wherein a recess is provided in said outer wall of said lower housing part and in said inner wall of said upper housing part, and the two recesses are opposite each other when said two housing parts are in a given rotary position, and a moveable blocking element is provided which is located initially only in the recess in said lower housing part and a push rod for moving said blocking element partially into the recess in said upper housing part to prevent the upper and lower housing parts from rotating relative to each other is provided which cooperates with said slider on said spindle of said counter.

An inhalation atomizer comprising a new blocking function through a locking mechanism and a new counter is presented in this invention, which has significant advantages over the prior arts and is able to limit the period of use of the inhalation atomizer so that safety requirements are meet. The limitation may be beneficial in terms of technical, medical or hygiene considerations.

After a predetermined number of actuations, the inhalation atomizer in the current invention will be appropriately blocked through a locking mechanism. The locking mechanism is realized mainly by two protrusions. Protrusion A is located on the outer wall of the lower unit of the inside part. Protrusion B is located on the inner wall of counter. When the atomizer is actuated each time, the counter will make a rotation with a constant angle around the lower unit of the inside part. Once the predetermined number of actuations is achieved, Protrusion A and Protrusion B will encounter with each other and hence the counter will be prevented from further rotation. Therefore the atomizer is blocked and stopped from further use. The number of actuations of the device can be counted by the counter.

SUMMARY OF THE INVENTION

The current invention is directed to an inhalation atomizer device or apparatus comprising a block function and a counter which will reliably, effectively and finally prevent further use of the apparatus after a given number of actuations if there is a compelling reason for this. After a predetermined number of actuations, the atomizer will be appropriately blocked through a locking mechanism. The locking mechanism is realized mainly by two protrusions. Protrusion A is located on the outer wall of the lower unit of the inside part. Protrusion B is located on the inner wall of counter. The lower unit of the inside part is nested in the counter. The counter can rotate relative to the lower unit of the inside part. Because of the rotation of the counter, the number displayed on the counter can change as the actuation number increases, and can be observed by the patient. After each actuation, the number displayed on the counter has a change. Once the predetermined number of actuations is achieved, Protrusion A and Protrusion B will encounter with each other and hence the counter will be prevented from further rotation. Therefore the atomizer is blocked and stopped from further use. The number of actuations of the device can be counted by the counter.

According to a first embodiment, the current invention is directed to an inhalation atomizer comprising a block function through locking mechanism. The locking function is realized according to the invention by an inhalation atomizer device having the following characterizing features:

Protrusion A is provided on the outer wall of the lower unit of the inside part and Protrusion B is provided on the inner wall of the counter. Two protrusions are on the same horizontal level.

A continuous indentation is provided on the counter so that the Protrusion B on the outer wall of the lower unit of the inside part can move rotatably in the indentation. Therefore the relative rotation between the counter and the lower unit of the inside part is feasible. After certain angles of rotation, the two protrusions will encounter with each other and hence further rotation will be prevented.

According to a second embodiment, the current invention is directed to a counter with a continuous indentation. A protrusion on the counter can be installed on the inner wall of the counter. In this embodiment of the current invention, the continuous indentation of the counter should be installed on the inner wall of the counter, and the two protrusions should be on the same horizontal level so that the relative rotation between the counter and the lower unit of the inside part is feasible. During the normal use of the atomizer, the protrusion of the lower unit of the inside part can move rotatably in the continuous indentation of the counter.

In preferred embodiment of the current invention, the protrusion of the counter can be installed on the top of the counter. In this situation, there is no need to have the continuous indentation on the counter. Instead the protrusion of the lower unit should be on the same horizontal level with the protrusion of the counter. During the normal use of the atomizer, the protrusion of the lower unit move rotatably at the top of the counter.

In a preferred embodiment of the current invention, the blocking elements may be protrusions on the wall of the counter and lower unit, preferably made by plastic materials.

The blocking function through the locking mechanism according to the current invention has the following advantages:

It is appropriate for miniaturized apparatus.

It is easy to assemble.

The protrusions are located on the inner wall of the counter and on the outer wall of the lower unit of the inside part. When the atomizer is used, the patient cannot access the protrusions because of their positions.

The predetermined number of actuations can be modified based on the positions of the counter when it is assembled. Therefore re-opening and injecting new mold is not required to adjust the predetermined number of actuations and hence the cost is saved.

Once the predetermined number of actuations is achieved, Protrusion A and Protrusion B will encounter with each other and hence the counter will be prevented from further rotation. Therefore the atomizer is blocked and stopped from further use.

The blocking function according to the current invention is used for example in a high pressure atomizer or in a needleless injector. A medical liquid administered using such a device may contain a drug dissolved in a solvent. Suitable solvents include, for example, water, ethanol or mixture thereof.

The third aspect of the current invention is further directed to an inhalation atomizer comprising the block function and the counter described above. The inhalation atomizer is preferably a portable and hand-held device for delivering the pharmaceutical formulation or medicaments to the patients through a soft mist inhalation. In a preferred embodiment of the current invention, when such inhalation atomizer is stressed or an intended dose delivery every time, a pre-determined amount of fluid is preferably released automatically.

In a preferred embodiment of the current invention, a precursory amount of fluid to be expelled before every actual dose to rinsing the nozzle is not required for the inhalation atomizer of the current invention. The inhalation atomizer comprising the locking function and the counter of the current invention can provide adequate fluids to deliver the full dose of the pre-determined dose numbers, even after allowing the inhalation atomizer to rinse the device system at least 5 times by expelling the full dose amount of the fluids before the actual dose to the patients. The dose numbers can alternatively be countered by a sensor or an electronic digital counter attached or integrated with the inhalation atomizer of the current invention.

DESCRIPTION OF THE INVENTIONS

According to a first embodiment, the current invention is directed to an inhalation atomizer device or apparatus which will reliably, effectively and finally prevent further use of the apparatus after a given number of actuations if there is a compelling reason for this. After a predetermined number of actuations, the atomizer will be appropriately blocked through a locking mechanism. The locking mechanism is realized mainly by two protrusions. Protrusion A is located on the outer wall of the lower unit of the inside part. Protrusion B is located on the inner wall of counter. The lower unit of the inside part is nested in the counter. The counter can rotate relative to the lower unit of the inside part. Because of the rotation of the counter, the number displayed on the counter can change as the actuation number increases, and can be observed by the patient. After each actuation, the number displayed on the counter has a change. Once the predetermined number of actuations is achieved, Protrusion A and Protrusion B will encounter with each other and hence the counter will be prevented from further rotation. Therefore the atomizer is blocked and stopped from further use. The number of actuations of the device can be counted by the counter.

According to a second embodiment, the current invention is directed to an inhalation atomizer with a block function through locking mechanism. The locking function is realized according to the invention by an inhalation atomizer device having the following characterizing features:

Protrusion A is provided on the outer wall of the lower unit of the inside part and Protrusion B is provided on the inner wall of the counter. Two protrusions are on the same horizontal level.

A continuous indentation is provided on the counter so that the Protrusion B on the outer wall of the lower unit of the inside part can move rotatably in the indentation. Therefore the relative rotation between the counter and the lower unit of the inside part is feasible. After certain angles of rotation, the two protrusions will encounter with each other and hence further rotation will be prevented.

The blocking function through the locking mechanism according to the current invention has the following advantages:

It is appropriate for miniaturized apparatus.

It is easy to assemble.

The protrusions are located on the inner wall of the counter and on the outer wall of the lower unit of the inside part. When the atomizer is used, the patient cannot access the protrusions because of their positions.

The predetermined number of actuations can be modified based on the positions of the counter when it is assembled. Therefore re-opening and injecting new mold is not required to adjust the predetermined number of actuations and hence the cost is saved.

Once the predetermined number of actuations is achieved, Protrusion A and Protrusion B will encounter with each other and hence the counter will be prevented from further rotation. Therefore the atomizer is blocked and stopped from further use.

The blocking function according to the current invention is used for example in a high pressure atomizer or in a needleless injector. A medical liquid administered using such a device may contain a drug dissolved in a solvent. Suitable solvents include, for example, water, ethanol or mixture thereof.

Figure 2:
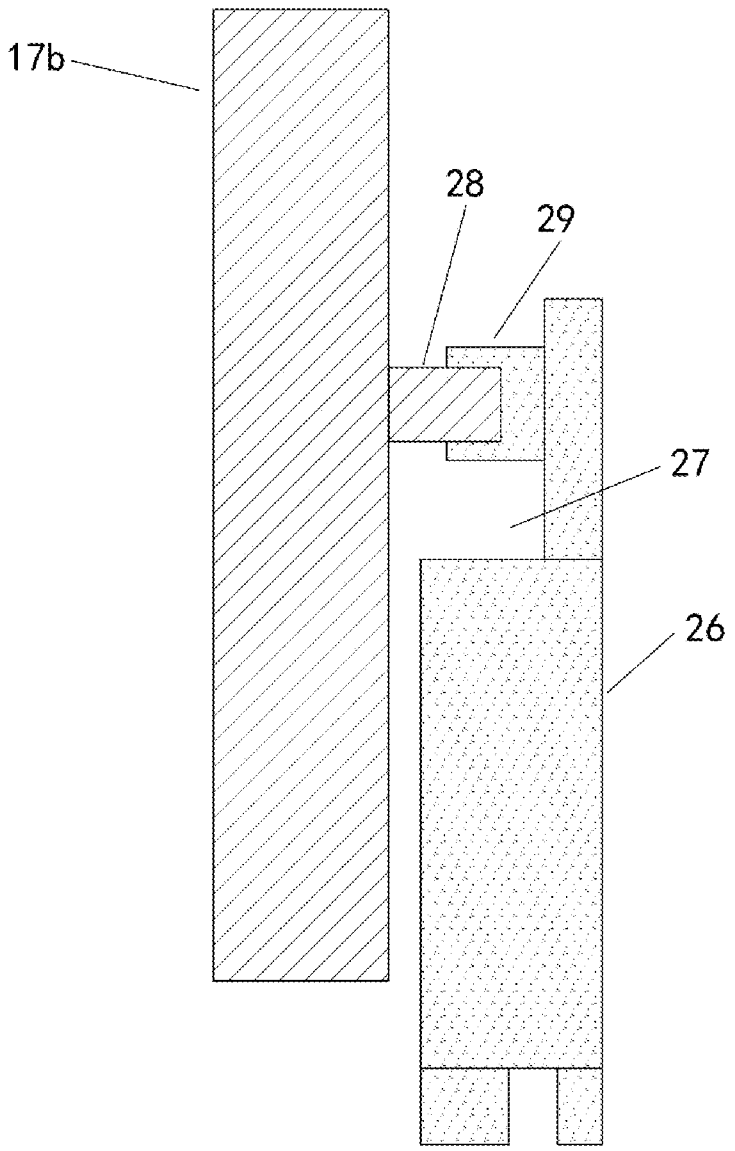

FIGS. 1 and 2 demonstrate a preferred embodiment of the blocking function according to the current invention. These two figures show partial longitudinal sections through the wall of the lower unit 17*b* and the counter 26. The longitudinal sections run parallel to the axis of the lower unit 17*b* and the counter 26.

In FIG. 1, the atomizer is in the un-locking state. The lower unit 17*b* of the inside part 17 is nested in the counter 26. The relative rotation between the lower unit 17*b* and the counter 26 is feasible. On the inner of the counter 26, there is a continuous indentation 27 and a protrusion B 29 (which is not showed in the FIG. 1). There is also a protrusion A 28 on the outer of the lower unit 17*b*, which is on the same horizontal level with the protrusion B 29 and can move rotatably in the continuous indentation 27. When the atomizer is actuated each time, the counter 26 will make a rotation with a constant angle around the lower unit 17*b*. As the actuation number is increasingly close to the predetermined number of actuations, the protrusions A and B are getting closer and closer. Until when the predetermined number of actuations is reached, the protrusions A and B encounter with each other, namely the locking state showed in the FIG. 2. Therefore the counter will be prevented from further rotation and hence the atomizer is locked and stopped from further use.

According to a second embodiment, the current invention is directed to a counter with a continuous indentation. A protrusion on the counter can be installed on the inner wall of the counter. In this embodiment of the current invention, the continuous indentation of the counter should be installed on the inner wall of the counter, and the two protrusions should be on the same horizontal level so that the relative rotation between the counter and the lower unit of the inside part is feasible. During the normal use of the atomizer, the protrusion of the lower unit of the inside part can rotate around in the continuous indentation of the counter.

In preferred embodiment of the current invention, the protrusion of the counter can be installed on the top of the counter. In this situation, there is no need to have the continuous indentation on the counter. Instead the protrusion of the lower unit should be on the same horizontal level with the protrusion of the counter. During the normal use of the atomizer, the protrusion of the lower unit can rotate around at the top of the counter.

Figure 5:
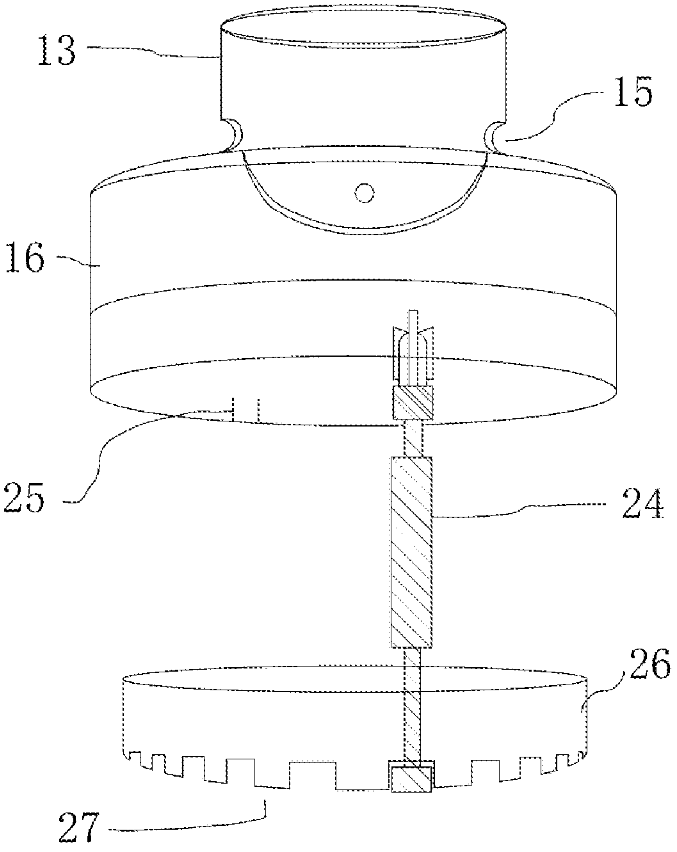

The atomizer 1 preferably includes a counter element showed in FIG. 5. The counter element has a worm 24 and a counter ring 26. The counter ring 26 is preferred circular and has dentate part at the bottom. The worm 24 has upper and lower end gears. The upper end gear contacts with the upper shell 16. The upper shell 16 has inside bulge 25. When the atomizer 1 is employed, the upper shell 16 rotates; and when the bulge 25 passes through the upper end gear of the worm 24, the worm 24 is driven to rotate. The rotation of the worm 24 drives the rotation of the counter ring 26 through the lower end gear. Then it results in the counting effect.

The third aspect of the current invention is further directed to an inhalation atomizer device as well as a procedure and/or an operation of the inhalation atomizer comprising the blocking function and the counter described above. Through easy and simple steps and operations of this inhalation device, an accurate metering of the inhalation aerosol could be achieved.

The third aspect of the current invention is further directed to an inhalation atomizer comprising the block function and the counter described above. The inhalation atomizer is preferably a portable and hand-held device for delivering the pharmaceutical formulations or medicaments to the patients through a soft mist inhalation. In a preferred embodiment of the current invention, a precursory amount of fluid to be expelled before every actual dose to rinsing the nozzle is not necessary for the inhalation atomizer of the current invention. The locking function and the counter in the current invention can provide adequate or enough fluids to deliver the pre-determined doses, even after allowing the inhalation atomizer to rinse the device system at least 3 times by expelling the full dose amount of the fluids before the actual dose. The dose numbers can alternatively be countered or tracked by a touch sensor or an electronic digital counter attached or integrated with the atomizer of the current invention.

Figure 6:
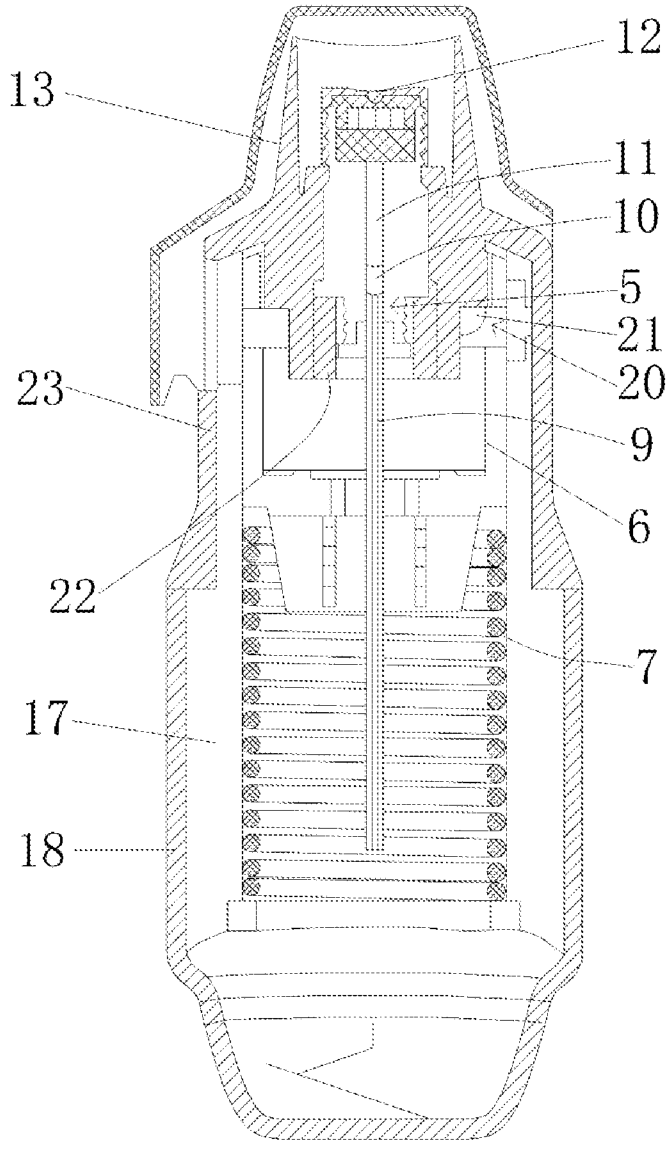

A typical example of the inhalation atomizer 1 comprising the block function and the counter described above of the current invention is shown in FIG. 3, FIG. 4 and FIG. 6. The current invention of the atomizer 1 comprising the block function and the counter described above includes, but not limited to, the inhalation device provided in FIG. 3, FIG. 4 and FIG. 6. The current invention of the atomizer 1 comprising the block function and the counter described above further comprises the inhalation atomizer device which can be modified from these presented in FIG. 3, FIG. 4 and FIG. 6. FIG. 6 shows the picture of the device features inside the inhalation atomizer 1 from the 3D drawing.

Figure 3:
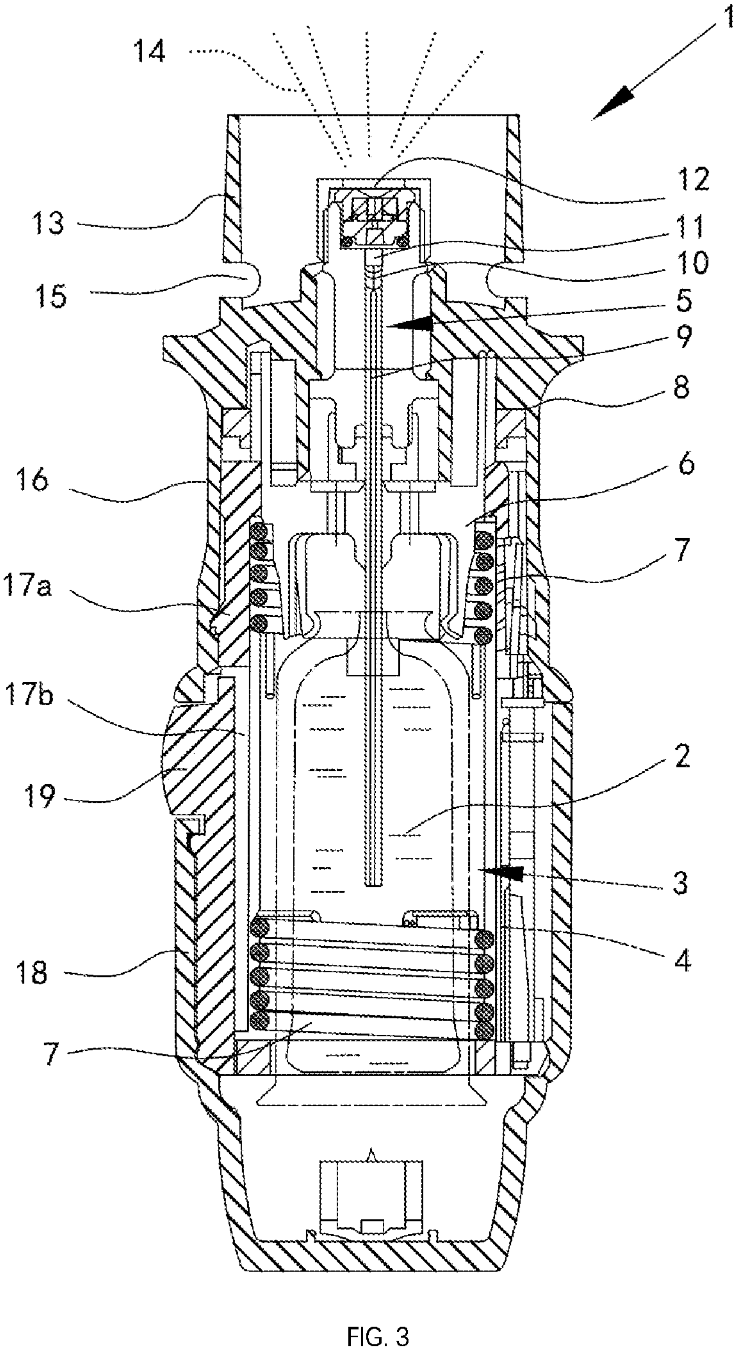
Figure 4:
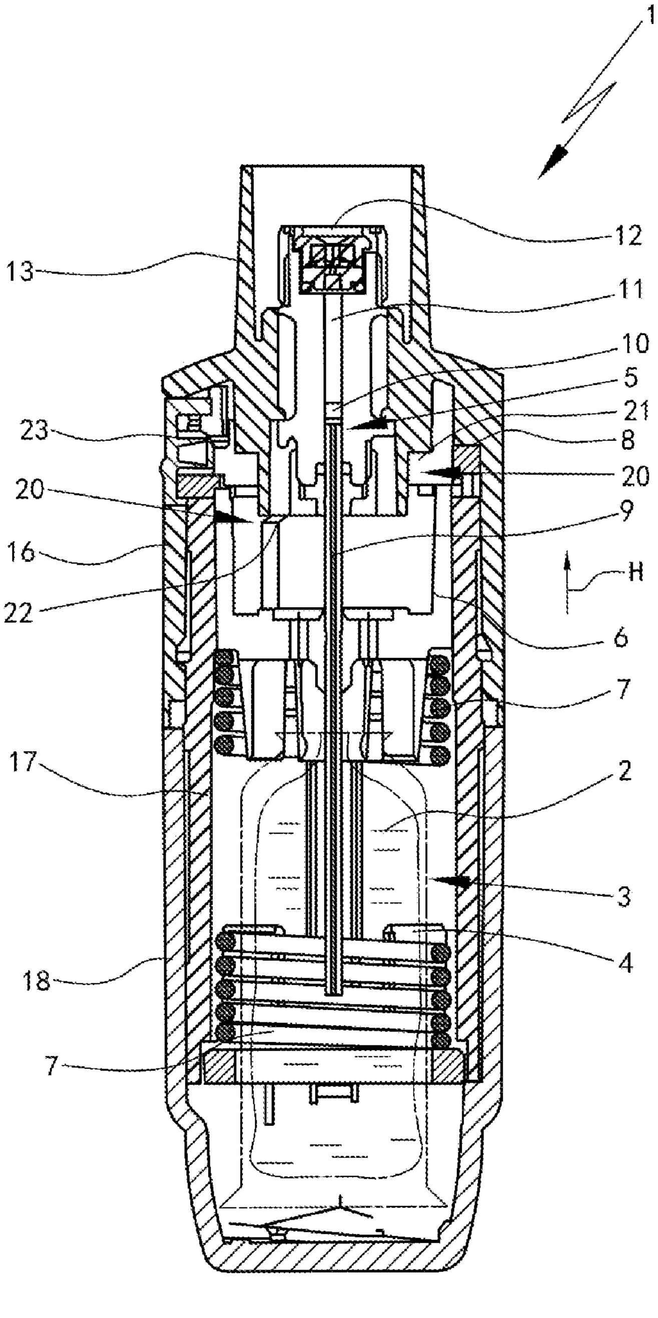

A typical example of the inhalation atomizer 1 comprising the block function and the counter described above for spraying a medicament fluid 2 is demonstrated in the FIG. 3 as non-stressed state and in the FIG. 4 as stressed state. The atomizer 1 comprising the block function and the counter described above is preferred as a portable inhaler and requires no propellant gas.

For the typical atomizer 1 comprising the block function and the counter described above, an aerosol 14 that can be inhaled by a patient is generated through the atomization of the fluid 2, which is preferred formulated as a medicament liquid. The medicament is typically administered at least once a day, more specifically multiple times a day, preferred at predestined time gaps, according to how serious the illness affects the patient.

A preferred atomizer 1 comprising the block function and the counter described above has substitutable and insertable vessel 3, which contains the medicament fluid 2. Therefore, a reservoir for holding the fluid 2 is formed in the vessel 3. Specifically, the medicament fluid 2 is located in the fluid compartment 4 formed by a collapsible bag in the vessel 3.

A preferred adequate amount of fluid 2 for the inhalation atomizer 1 comprising the block function and the counter described above is in the vessel 3 to provide, i.e., up to 200 doses. A classical vessel 3 has a volume of 2 to 10 ml. A pressure generator 5 in the atomizer 1 is used to deliver and atomize the fluid 2, specifically in a predestined dosage amount. Therefore, the fluid 2 could be released and sprayed in individual doses, specifically from 5 to 30 microliter.

The typical atomizer 1 comprising block function and the counter described above may preferably have a pressure generator 5 and a holder 6, a drive spring 7, and a locking part 8 which is preferred manually operated to discharge it, a delivering tube 9, a non-return valve 10, a pressure room 11, and a nozzle 12 in the area of a mouthpiece 13. The vessel 3 is latched by the holder 6 in the atomizer 1 so that the delivering tube 9 is plunged into the vessel 3. The vessel 3 could be separated from the atomizer 1 for substitution.

For the atomizer 1 comprising block function and the counter described above, when drive spring 7 is stressed in axial direction, the delivering tube 9, the vessel 3 along with the holder 6 will be shifted downwards. Then the fluid 2 will be sucked into the pressure room 11 through delivering tube 9 and the non-return valve 10.

For the inhalation atomizer 1 comprising the block function and the counter described above, after the locking part 8 is actuated to release the holder 6, then the stress is eased. During this process, the delivering tube 9 and closed non-return valve 10 are shifted back upward by releasing the drive spring 7. Consequently, the fluid 2 is under the pressure in the pressure room 11. Then the fluid 2 is pushed through the nozzle 12 and atomized into an aerosol 14 by the pressure. A patient could inhale the aerosol 14 through the mouthpiece 13, while the air is sucked into the mouthpiece 13 through air inlets 15.

The inhalation atomizer 1 comprising the block function and the counter described above has an upper shell 16. Then an inside part 17, which could be rotated relative to the upper shell 16, has an upper unit 17*a* and a lower unit 17*b*. A lower shell 18 is manually operable to attach onto the inside part 17 preferred through the holding unit 19. The lower shell 18 could be separated from the atomizer 1 so that the vessel 3 could be substituted and inserted.

The inhalation atomizer 1 comprising the block function and the counter described above may preferably have the lower shell 18, which carries the inside part 17, is rotatable relative to the upper shell 16. As a result of rotation and engagement between the upper unit 17*a* and the holder 6, through a gear 20, the holder 6 is axially moved the counter to the force of the drive spring 7 and the drive spring 7 is stressed.

In the typical stressing state, the vessel 3 is shifted downwards and reaches to a final position, which is demonstrated in the FIG. 4. The drive spring 7 is stressed under this final position. Then the holder 6 is clasped by the locking part 8. Therefore, the vessel 3 and the delivering tube 9 are prevented from moving upwards so that the drive spring 7 is stopped from easing.

The typical atomizing process occurs after the locking part 8 releases the holder 6. The vessel 3, the delivering tube 9 and the holder 6 are shifted back by the drive spring 7 to the beginning position in the FIG. 3. This is described as major shifting in here. While the major shifting occurs, the non-return valve 10 is closed and the fluid 2 is under the pressure in the pressure room 11 by the delivering tube 9, and then the fluid 2 is pushed out and atomized by the pressure.

The inhalation atomizer 1 comprising the block function and the counter described above may preferably have a clamping function. During the clamping, the vessel 3 preferably performs a lifting shift or for the withdrawal of the fluid 2 during the atomizing process. The gear 20 has sliding surfaces 21 and 22 on the upper shell 16 and/or on the holder 6, which could make holder 6 axially move when the holder 6 is rotated relative to the upper shell 16.

In this clamping function, when the holder 6 is in the clamping position (FIG. 4), the sliding surfaces 21 and 22 move out of engagement. Then the gear 20 releases the holder 6 for the opposite shift axially. Meanwhile, the locking part 8 changes into locking position so that the delivering tube 9, the vessel 3 and the holder 6 are in the stressing state. In particular the locking part 8 is of annular construction and in its locking position is radically shifted out of the normally concentric arrangement with the holder 6 so that the holder 6 abuts with its end face on a portion of the locking part 8 and is blocked thereby.

The inhalation atomizer 1 comprising the block function and the counter described above may preferably have the locking part 8 which may be actuated by a button 23 to shift back to its concentric position so that the atomizing process is activated. The holder 6 may be not blocked for too long and can carry on the major shifting. Therefore, the fluid 2 is pushed out and atomized.

Nevertheless, the drug formulation solution presented in the current invention may also be applied to other atomizers or inhalers, including powder inhalers, metered dose inhalers and so forth.

The atomizer 1 comprising the block function and the counter described above is specifically devised to spray medicament aerosol 14 as an inhaler. Still, it can also be devised for cosmetic use with the adjustment on the content in the vessel 3, specifically as a perfume atomizer.

The fluid 2 is preferably a liquid, specifically an aqueous medicine or ethanolic medicine formulation. Nevertheless, it may also be applied for other types of formulation such as suspensions or powders.

According to the current invention the preferred pharmaceutical active ingredients and/or formulations of the preferred fluid 2 are listed below. The pharmaceutical active ingredients may be formulated as aqueous or non-aqueous solutions, mixtures, ethanol-containing or solvent-free formulations.

In preferred aspect of the current invention, the fluid 2 used in the inhalation atomizer device comprising the block function and the counter described above comprises the compounds as single pharmaceutical ingredient active or in combination of two or more pharmaceutical ingredient actives. The pharmacologically active substance is preferably selected from among the betamimetics, anticholinergics, corticosteroids, PDE4-inhibitors, LTD4-antagonists, EGFR-inhibitors, dopamine agonists, H1-antihistamines, PAF4-antagonists and PI3-kinase inhibitors. Moreover, double or triple combinations of W may be combined and used in the device according to the invention. Combinations of the pharmaceutical active ingredient might be, for example:

A betamimetic, combined with an anticholinergic, corticosteroid, PDE4-inhibitor, EGFR-inhibitor or LTD4-antagonist, An anticholinergic, combined with a betamimetic, corticosteroid, PDE4-inhibitor, EGFR-inhibitor 60 or LTD4-antagonist, A corticosteroid, combined with a PDE4-inhibitor, EGFR-inhibitor or LTD4-antagonist, A PDE4-inhibitor, combined with an EGFR-inhibitor or LTD4-antagonist An EGFR-inhibitor, combined with an LTD4-antagonist.

In a more specifically preferred aspect of the current invention, the compounds and their pharmaceutically acceptable salts used as betamimetics the fluid 2 used in the inhalation atomizer device comprising the block function and the counter described above are preferably selected from among vilanterol, olodaterol, indacaterol, albuterol, arformoterol, bambuterol, bitolterol, broxaterol, carbuterol, clenbuterol, fenotrol, formoterol, metaprotereol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethylindan-2-ylamino)-1-hydroxy-ethyl]-8-hydroxy-1H-quinolin-2-one, 4-hydroxy-7-[2-{[2-{[3-(2-phenylethoxy)propyl] sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butyl amino]ethanol, 1-[2H-5-hydroxy-3-oxo-4H-1,4-benzoxazin-8-yl]-2-[3-(4-N,N-dimethylaminophenyl)-2-methyl-2-propylamino] ethanol, 1-[2H-5-hydroxy-3-oxo-4H-1,4-benzoxazin-8-yl]-2-[3-(4-methoxyphenyl)-2-methyl-2-propyl amino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylaminoethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo [1,4] oxazin-3-one, 6-hydroxy-8-{1-hydroxy-2-[2-(ethyl-4-phenoxy-acetate)-1,1-dimethyl-ethylamino]-ethyl}-4 H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo [1, 4]oxazin-3-one, 6-hydroxy-8-{1-hydroxy-2-[2-(4-hydroxy-phenyl)-1,1-dimethyl-ethylamino]-ethyl}-4H-benzo[1,4] oxazin-3-one, 6-hydroxy-8-{1-hydroxy-2-[2-(4-isopropyl-phenyl)-1,1-dimethyl-ethylamino]-ethyl}-4H-benzo [1,4] oxazin-3-one 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-pheyl)-1,1-dimethyl-ethylamino]-1-hydroxy-ethyl}-6-hydroxy-4H-benzo [1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo [1,4] oxazin-3-one, 1-(4-ethoxy-carbonylamino-3-cyano-5-fluorophenyl)-2-(tert-butylamino)ethanol, 2-hydroxy-5-(1-hydroxy-2-{2-[4-(2-hydroxy-2-phenyl-ethylamino)-phenyl]-ethylamino}-ethyl)-benzaldehyde, N-[2-hydroxy-5-(1-hydroxy-2-{2-[4-(2-hydroxy-2-phenyl-ethylamino)-phenyl]-ethylamino}-ethyl)-phenyl]-formamide, 8-hydroxy-5-(1-hydroxy-2-{2-[4-(6-methoxy-biphenyl-3-ylamino)-phenyl]-ethylamino}-ethyl)-1 H-quinolin-2-one, 8-hydroxy-5-[1-hydroxy-2-(6-phenethylamino-hexylamino)-ethyl]-1H-quinolin-2-one, 5-[2-(2-{4-[4-(2-amino-2-methyl-propoxy)-phenylamino]-phenyl}-ethylamino)-1-hydroxy-ethyl]-8-hydroxy-1H-quinolin-2-one,

[3-(4-{6-[2-hydroxy-2-(4-hydroxy-3-hydroxymethyl-phenyl)-ethylamino]-hexyloxy}-butyl)-5-methyl-phenyl]-urea, 4-(2-{6-[2-(2,6-dichloro-benzyloxy)-ethoxy]-hexylamino}-1-hydroxy-ethyl)-2-hydroxymethyl-phenol, 3-(4-{6-[2-hydroxy-2-(4-hydroxy-3-hydroxymethyl-phenyl)-ethylamino]-hexyloxy}-butyl)-benzylsulphonamide, 3-(3-{7-[2-hydroxy-2-(4-hydroxy-3-hydroxymethyl-phenyl)-ethylamino]-heptyloxy}-propyl)-benzylsulphonamide, 4-(2-{6-[4-(3-cyclopentanesulphonyl-phenyl)-butoxy]-hexylamino}-1-hydroxy-ethyl)-2-hydroxymethyl-phenol, N-adamantan-2-yl-2-(3-{2-[2-hydroxy-2-(4-hydroxy-3-hydroxymethyl-phenyl)-ethylamino]-propyl}-phenyl)-acetamide, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In a more specifically preferred aspect of the current invention, the anticholinergics used in the fluid 2 of the inhalation atomizer device comprising the block function and the counter described above are preferably selected from among aclidinium salts, preferably the bromide salt, umeclidinium salts, preferably the bromide salt, the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

AC-1

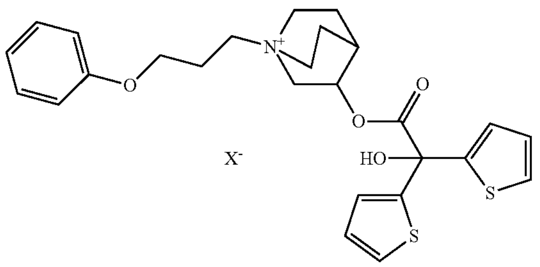

wherein X— denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en AC-1-en

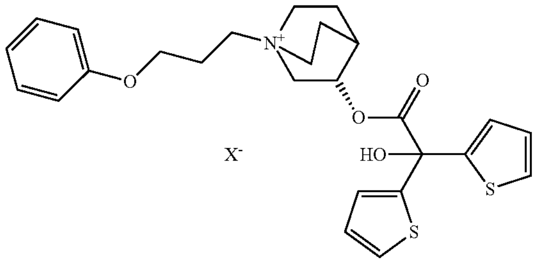

wherein X— may have the above-mentioned meanings. Other preferred anticholinergics are selected from the salts of formula AC-2

AC-2

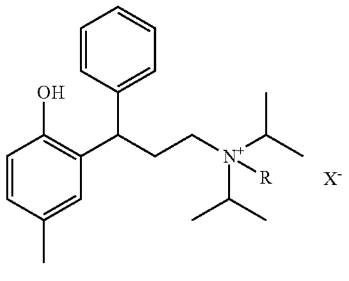

wherein R denotes either methyl or ethyl and wherein X— may have the above-mentioned meanings. In an alternative embodiment the compound of formula AC-2 may also be present in the form of the free base AC-2-base.

AC-2-base

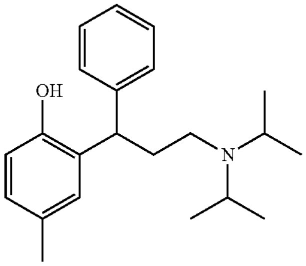

In another preferred aspect of the current invention, specified compounds are selected from tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide; tropenol 3,3,4,4,-tetrafluorobenzilate methobromide, scopine 3,3'4,4'-tetrafluorobenzilate methobromide; tropenol 4,4'-difluorobenzilate methobromide, scopine 4,4'-difluorobenzilate methobromide, tropenol 3,3'-difluorobenzilate methobromide, scopine 3,3,-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylatemethobromide, tropenol 9-methyl-xanthene-9-carboxylate methobromide, scopine 9-methyl-xanthene-9-carboxylate methobromide, tropenol, 9-ethyl-xanthene-9-carboxylatemethobromide, tropenol 9-difluoromethyl-xanthene-9-carboxylatemethobromide. The above-mentioned compounds may also be used as salts within the scope of the present invention.

In a more preferred aspect of the current invention, the corticosteroids used in the fluid 2 of the inhalation atomizer device comprising the block function and the counter described above are selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, (S)-fluoromethyl-6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

In a more specifically preferred aspect of the current invention, the corticosteroids used in the fluid 2 of the inhalation atomizer device comprising the block function and the counter described above are selected from fluticasone propionate and fluticasone furoate.

PDE4-inhibitors used in the fluid 2 of the inhalation atomizer device comprising the block function and the counter described above are preferably selected from compounds among enprofyllin, theophyllin, roflumilast, ariflo (cilomilast), tofimilast, pumafentrin, lirimilast, 60 arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N,-[N-2-cyano-S-methyl-isothioureido]benzyl)-2-pyrrolidone, cis[4-cyano-4-(3-cyclopentyloxy-4-methoxyphenyl)cyclohexane-1-carboxylic acid]2-carbomethoxy-4-cyano-4-(3-cyclopropylmethoxy-4-difluoromethoxy-phenyl) cyclohexan-1-one, cis[4-cyano-4-(3-cyclopropylmethoxy-4-difluoromethox-yphenyl)cyclohexan-1-ol] (R)-(+)-ethyl [4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrzolo [3,4-c]-1,2,4-triazolo [4,3-a]pyridine, 9-cyclopentyl-5,6-dihydro-7-ethyl-3-(tert-butyl)-9H-pyrazolo [3,4-c]-1,2,4-triazolo [4,3-a] pyridine, optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used in the fluid 2 of the inhalation atomizer device comprising the block function and the counter described above are preferably selected from compounds of zileuton, montelukast, pranlukast, zafirlukast, MCC-847 (ZD-3523), MN-001, MEN-91507, (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio) methylcyclopropane-acetic acid, 1-(((1R)-3-3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid, [2-[[2-(4-tert-butyl-2-thiazolyl)-5-benzofuranyl]oxymethyl] phenyl acetic acid, optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydro sulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors used in the fluid 2 of the inhalation atomizer device comprising the block function and the counter described above are preferably selected from compounds of selected from among necitumumab, cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclo propyl methoxy-quinazoline, 4-[(3-chloro-4-fluorophenyl)amino]-6-{[4-(N,N-diethyl-amino)-1-oxo-2-buten-1-1]amino}-7-cyclopropyl-methoxy-quinazoline 4-[(3-chloro-4-fluorophenyl)amino]-6-{[4-(N,N-dimethyl amino)-1-oxo-2-buten-1-yl]amino}-7-cyclopropyl-methoxy-quinazoline, 4-[(R)-(1-phenyl-ethyl) amino]-6-{[4-(morpholin-4-yl)-1-oxo-2-buten-1-yl] amino}-7-cyclopentyl oxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-meth-oxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl) amino}-7-cyclopropylmethoxy-quinazoline, 4-[(3-chloro-4-fluorophenyl)amino]-6-{[4-(N,N-dimethy-lamino)-1-oxo-2-buten-1-yl]amino}-7-cyclopentyloxy-quinazoline, 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl) amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethy-lamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethy-lamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclo-pentyloxy-quinazoline, 4-[(3-chloro-4-fluorophenyl)amino]-6-{[4-(N,N-dimethy-lamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethy-lamino)-1-oxo-2-buten-1-yl]amino}-7-[(S)-(tetrahydrofuran-2-yl) methoxy]-quinazoline, 4-[(3-ethynyl-phenyl)amino]-6,7-to-(2-methoxy-ethoxy)-quinazoline-[(3-chloro-4-fluorophenyl) amino]-7-[3-(morpholin-4-yl)-4propyloxy]-6-[(vinyl-carbonyl)amino]-quinazoline, 4-[(R)-(1-phenyl-ethyl)amino]-6-(4-hydroxy-phenyl)-7H-pyrrolo[2,3-d]

pyrimidine 3-cyano-4-[(3-chloro-4-fluorophenyl)amino]-6-{[4-(N,N-dimethylamino)-1-oxo-2-buten-1-yl]amino}-7-ethoxy-quinoline, ro-4-fluorophenyl)amino]-6-(1-cyan-piperidin-4-yloxy)-7-methoxy-quinazoline optionally in the form of the racemates, enantiomers, diastereomers thereof and optionally in the form of the pharmacologically acceptable acid addition salts, solvates or hydrates thereof.

According to the invention the acid addition salts of the betamimetics used in the fluid 2 of the inhalation atomizer device comprising the block function and the counter described above are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used in the fluid 2 of the inhalation atomizer device comprising the block function and the counter described above are preferably selected from compounds among bromocriptin, cabergoline, alpha-dihy-droergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydro-bromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines used in the fluid 2 of the inhalation atomizer device comprising the block function and the counter described above are preferably selected from compounds among desloratadine, olopatadine, azelastine, epinastine, cetirizine, azelas-tine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydro-bromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, the compound used in the fluid 2 of the inhalation atomizer device comprising the block function and the counter described above are preferably selected from the groups of ergot alkaloid derivatives, the triptans, the CGRP-inhibitors, the phosphodiesterase-V inhibitors, interleukin-5 antagonists, kinase inhibitors, anti-PD-1, endothelin receptor antagonists, antibiotics, surfactants, anti-IgE, mast cell stabilizers, anti-RSV, CFTR-relevant compounds, IPF treatments, sGC stimulators, vasodilators, Alpha-Proteinase Inhibitors, antiarrhythmic, enzymes, sclerosing agents optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

Examples of interleukin-5 antagonists are reslizumab and mepolizumab.

Examples of kinase inhibitors are alectinib, osimertinib, nintedanib, ceritinib, crizotinib and gefitinib.

Examples of anti-PD-1 are pembrolizumab and nivolumab.

Examples of endothelin receptor antagonists are macitentan, ambrisentan and bosentan.

Examples of antibiotics are telavancin, bedaquiline, aztreonam, ceftaroline, tigecycline, telithromycin, moxifloxacin, clarithromycin, ceftibuten, piperacillin, tazobactam, amoxicillin/clavulanate, sparfloxacin, grepafloxacin, cefdinir, ciprofloxacin, cefuroxime, dirithromycin, Gatifloxacin, ertapenem, Cefazolin, rifapentine and tobramycin.

Examples of surfactants are lucinactant, calfactant and poractant alpha.

Example of phosphodiesterase-V inhibitors is tadalafil.

Example of anti-IgE is omalizumab.

Examples of mast cell stabilizers are nedocromil and cromolyn.

Example of anti-RSV is palivizumab.

Examples of CFTR-relevant compounds are lumacaftor and ivacaftor.

Example of IPF-treatments is pirfenidone.

Example of sGC stimulators is riociguat.

Example of vasodilators is treprostinil.

Examples of antiarrhythmic are dofetilide and verapamil.

Examples of enzymes are dornase alfa and laronidase.

Example of sclerosing agents is sterile talc.

Preferably, the current invention provides an inhalation atomizer device comprising a locking function and a counter described above which can accommodate the liquid pharmaceutical compositions for multiple doses in a container or cartridge, wherein the fluid 2 pharmaceutical composition comprises aclidinium bromide, formoterol fumarate, indacaterol maleate, glycopyrrolate bromide, fluticasone furoate, vilanterol trifenatate, umeclininium bromide, tiotropium bromide, olodaterol hydrochloride, ipratropium bromide or albuterol sulfate, including any their pharmaceutically acceptable salts, or any their combination as the active ingredient(s).

More preferably, the current invention provides an inhalation atomizer device comprising a locking function and a counter described above which can accommodate the liquid pharmaceutical compositions for multiple unit doses in a container or cartridge, wherein the pharmaceutical composition comprising a combination of aclidinium bromide and formoterol fumarate or any their pharmaceutically acceptable salts as the active ingredients.

More preferably, the current invention provides an inhalation atomizer device comprising a lock function and a counter described above which can accommodate the liquid pharmaceutical compositions for multiple unit doses in a container or cartridge, wherein the pharmaceutical composition comprising a combination of indacaterol maleate and glycopyrrolate bromide or any their pharmaceutically acceptable salts as the active ingredients.

More preferably, the current invention provides an inhalation atomizer device comprising a locking function described above which can accommodate the liquid pharmaceutical compositions for multiple unit doses in a container or cartridge, wherein the pharmaceutical composition comprising a combination of fluticasone furoate and vilanterol trifenatate or any their pharmaceutically acceptable salts as the active ingredients.

More preferably, the current invention provides an inhalation atomizer device comprising a locking function described above which can accommodate the liquid pharmaceutical compositions for multiple unit doses in a container or cartridge, wherein the pharmaceutical composition comprising a combination of vilanterol trifenatate and umeclininium bromide or any their pharmaceutically acceptable salts as the active ingredients.

More preferably, the current invention provides an inhalation atomizer device comprising a locking function described above which can accommodate the liquid pharmaceutical compositions for multiple unit doses in a container or cartridge, wherein the pharmaceutical composition comprising a triple combination of fluticasone furoate, vilanterol trifenatate and umeclininium bromide or any their pharmaceutically acceptable salts as the active ingredients.

More preferably, the current invention provides an inhalation atomizer device comprising a locking function described above which can accommodate the liquid pharmaceutical compositions for multiple unit doses in a container or cartridge, wherein the pharmaceutical composition comprising a combination of tiotropium bromide and olodaterol hydrochloride or any their pharmaceutically acceptable salts as the active ingredients.

More preferably, the current invention provides an inhalation atomizer device comprising a locking function described above which can accommodate the liquid pharmaceutical compositions for multiple unit doses in a container or cartridge, wherein the pharmaceutical composition comprising a combination of ipratropium bromide and albuterol sulfate or any their pharmaceutically acceptable salts as the active ingredients.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" or "pharmaceutical formulation" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

FIG. 1: A Schematic View of the Blocking Function in Non-locking State

FIG. 2: A Schematic View of the Blocking Function in Locking State

FIG. 3: A Schematic View of the Atomizer in Non-Stressed State

FIG. 4: A Schematic View of the Atomizer in Stressed State After Rotation Through 90 Degree as Related to FIG. 1

FIG. 5: A Schematic View of Counter Element of the Atomizer

FIG. 6: A Schematic View of the Atomizer from 3D Drawing

LIST OF REFERENCE NUMERALS

1: Atomizer
2: Fluid
3: Vessel
4: Fluid Compartment
5: Pressure Generator
6: Holder
7: Drive spring
8: Locking part
9: Delivering tube
10: Non-return valve
11: Pressure room
12: Nozzle
13: Mouthpiece
14: Aerosol
15: Air Inlet
16: Upper Shell
17: Inside Part
**17*a***: Upper Unit
**17*b***: Lower Unit
18: Lower Shell
19: Holding Unit
20: Gear
21: Sliding Surface
22: Sliding Surface
23: Button
24: Worm
25: Bulge
26: Counter
27: Continuous Indentation
28: Protrusion A
29: Protrusion B
H major shifting
S stressing shifting

I claim:

1. An inhalation atomizer comprising:

(a) a counter comprising a worm, a counter ring, and an upper shell, wherein the counter ring is circular with a bottom having an indentation, the worm has an upper end gear and a lower end gear, which contact the upper shell, and the upper shell comprises an inside bulge, and when the bulge passes through the upper end gear of the worm, the worm is driven to rotate, which drives rotation of the counter ring through the lower end gear, resulting in a counting effect;

(b) a blocking function comprising a locking mechanism which comprises a lower unit, wherein a lower unit comprises (i) a first protrusion which is nested in the indentation of the counter ring and (ii) a second protrusion, wherein the first protrusion and second protrusion are on the same horizontal level and able to move and rotate in the indentation, such that when the inhalation atomizer is actuated, the counter ring rotates around the lower unit with a constant angle, and when the first and second protrusions encounter each other, the counter is prevented from further rotation, locking the atomizer and stopping it from further use;

(c) a fluid in a vessel;

(d) a nozzle for the delivery and atomization of the fluid, wherein the fluid is delivered in metered individual full-doses; and (e) a delivering element in the form of a delivering tube, which is movable for delivering and atomizing the fluid.

2. The inhalation atomizer according to claim 1, wherein the fluid contains a solvent.

3. The atomizer according to claim 1, wherein the fluid comprises a pharmaceutical active ingredient selected from the group consisting of anticholinergics, betamimetics, steroids, phosphodiesterase IV-inhibitors, LTD4-antagonists and EGFR-kinase-inhibitors, antiallergics, ergot alkaloid derivatives, triptans, CGRP-antagonists, phosphodiesterase-V-inhibitors, and any combination of the foregoing.

4. The inhalation atomizer according to claim 1, wherein the fluid comprises a pharmaceutical active ingredient selected from the group consisting of aclidinium bromide, formoterol fumarate, indacaterol maleate, glycopyrrolate bromide, fluticasone furoate, vilanterol trifenatate, umeclidinium bromide, tiotropium bromide, olodaterol hydrochloride, ipratropium bromide, albuterol sulfate, any pharmaceutically acceptable salts thereof, and any combination thereof.

5. The inhalation atomizer according to claim 1, wherein the fluid comprises a pharmaceutical active ingredient selected from the group consisting of a combination of aclidinium bromide and formoterol fumarate.

6. The inhalation atomizer according to claim 1, wherein the fluid comprises a pharmaceutical active ingredient selected from the group consisting of a combination of indacaterol maleate and glycopyrrolate bromide, and any pharmaceutically acceptable salts thereof.

7. The inhalation atomizer according to claim 1, wherein the fluid comprises a pharmaceutical active ingredient selected from the group consisting of a combination of fluticasone furoate and vilanterol trifenatate.

8. The inhalation atomizer according to claim 1, wherein the fluid comprises a pharmaceutical active ingredient selected from the group consisting of a combination of fluticasone furoate, vilanterol trifenatate and umeclidinium bromide, and any pharmaceutically acceptable salts thereof.

9. The inhalation atomizer according to claim 1, wherein the fluid comprises a pharmaceutical active ingredient selected from the group consisting of tiotropium bromide and any pharmaceutically acceptable salts thereof.

10. The inhalation atomizer according to claim 1, wherein the fluid comprises a pharmaceutical active ingredient selected from the group consisting of a combination of tiotropium bromide and olodaterol hydrochloride, and any pharmaceutically acceptable salts thereof.

11. The inhalation atomizer according to claim 1, wherein the fluid comprises a pharmaceutical active ingredient selected from the group consisting of olodaterol hydrochloride and any pharmaceutically acceptable salts thereof.

12. The inhalation atomizer according to claim 1, wherein the fluid comprises a pharmaceutical active ingredient selected from the group consisting of a combination of ipratropium bromide and albuterol sulfate, and any pharmaceutically acceptable salts thereof.

13. A method for inhalation delivery of an atomized fluid in individual, metered full-doses through a nozzle, comprising atomizing a fluid with the inhalation atomizer of claim 1.

14. A blocking function comprising a locking mechanism and a counter, wherein:

(a) the counter comprises a worm and a counter ring, wherein the counter ring is circular having a bottom with a continuous indentation, the worm has an upper end gear and a lower end gear that contact an upper shell, and the upper shell comprises an inside bulge, such that when the bulge passes through the upper end gear of the worm, the worm is driven to rotate, which drives rotation of the counter ring through the lower end gear, resulting in a counting effect; and (b) the blocking function comprises a lower unit, which comprises (i) a first protrusion which is nested in the continuous indentation of the counter ring and (ii) a second protrusion, wherein the first protrusion and second protrusion are on the same horizontal level and able to move and rotate in the continuous indentation, such that when the inhalation atomizer is actuated, the counter ring rotates around the lower unit with a constant angle, and when the first and second protrusions encounter each other, the counter is prevented from further rotation, locking the atomizer and stopping it from further use.

* * * * *